(12) United States Patent
Muzykantov et al.

(10) Patent No.: US 7,041,287 B2
(45) Date of Patent: May 9, 2006

(54) COMPOSITIONS AND METHODS FOR SELECTIVE DISSOLUTION OF NASCENT INTRAVASCULAR BLOOD CLOTS

(75) Inventors: Vladimir R. Muzykantov, Warwick, PA (US); Juan Carlos Murciano, Sevilla (ES); Douglas Cines, Wynnewood, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 313 days.

(21) Appl. No.: 10/611,723

(22) Filed: Jul. 1, 2003

(65) Prior Publication Data

US 2004/0053408 A1 Mar. 18, 2004

Related U.S. Application Data

(60) Continuation-in-part of application No. 10/253,518, filed on Sep. 23, 2002, which is a division of application No. 09/454,666, filed on Dec. 3, 1999, now Pat. No. 6,488,927, which is a continuation-in-part of application No. PCT/US99/10547, filed on May 12, 1999.

(60) Provisional application No. 60/086,262, filed on May 21, 1998.

(51) Int. Cl.
   C12N 9/70     (2006.01)
   C12N 9/72     (2006.01)
   C12N 9/96     (2006.01)
   A61K 38/49    (2006.01)

(52) U.S. Cl. .................. 424/94.3; 435/188; 436/519; 514/2

(58) Field of Classification Search ............... 424/94.3; 435/188 R; 436/514; 514/2
See application file for complete search history.

(56) References Cited

OTHER PUBLICATIONS

Kajihara et al., "Physiochemical characterization of PEG-PPG conjugated human urokinase", Biochimica et Biophysica Acta 1994 1199:202-208.
Muzykantov et al., "Regulation of the Complement-Mediated Elimination of Red Blood Cells Modified with Biotin and Streptavidin", Analytical Biochemistry 1996 241:109-119.
Bdeir et al., "Urokinase mediates fibrinolysis in the pulmonary microvasculature", Blood 2000 96(5):1820-1826.
Collen D., "Towards improved thrombolytic therapy", Lancet 1993 342:34-36.
Collen et al., "Mechanisms of activiation of mammalian plasma fibrinolytic systems with streptokinase and with recombinant staphylokinase", Eur. J. Biochem. 1993 216:307-314.
Fears R. and G. Poste, "Obstacles to the Development of Novel Thrombolytic Agents for Acute Myocardial Infarction Therapy : Is the Good the Enemy of the Best?", Fibrinolysis 1994 8:203-213.
Heeremans et al., "Thrombolytic Treatment with Tissue-type Plasminogen Activator (t-PA) Containing Liposomes in Rabbits:a Comparison with Free 5-PA", Throm. Haemost. 1995 73:488-494.
Holvoet et al., "Thrombolytic Profiles of Clot-Targeted Plasminogen Activators—Parameters Determining Potency and Initial Maximal Rates", Circulation 1993 87:1007-1016.
Kalofonos et al., "Imaging of Tumor in Patients with Indium-111-Labeled Biotin and Streptavidin-Conjugated Antibodies:Preliminary Communication", J. Nucl. Med. 1990 31:1791-1796.
Kinoshita K. and T. Tsong, "Survival of sucrose-loaded erythrocytes in the circulation", Nature 1978 272:258-260.
Krishnamurti et al., "PAI-1-Resistant t-PA:Low Doses Prevent Fibrin Deposition in Rabbits With Increased PAI-Activity", Blood 1996 87:14-19.
Lijnen R. and D. Collen, "Remaining Perspectives of Mutant and Chimeric Plasminogen Activators", Ann. NY Acad. Sci. 1992 667:357-364.
Murciano et al., "Platelets inhibit the lysis of pulmonary microemboli", Am. J. Physiol. Lung Cell Mol. Physiol, 2002 282:L529-L539.
Muzykantov et al., "Targeting of enzyme immobilized on erythrocyte membrane to collagen-coated surface", FEBS Lett. 1985 182:62-66.
Muzykantov et al., "Directed Targeting of Immunoerythrocytes Provides Local Protection of Endothelial Cells From Damage by Hydrogen Peroxide", Am. J. Pathol. 1987 128:276-285.
Muzykantov et al., "Avidin-induced lysis of biotinylated erythrocytes by homologous complement via the alternative pathway depends on avidin's ability of multipoint binding with biotinylated membrane", Biochim. Biophys. Acta 1992 1107:119-125.

(Continued)

Primary Examiner—Michael Borin
(74) Attorney, Agent, or Firm—Licata & Tyrrell P.C.

(57) ABSTRACT

Compositions and methods for prevention and treatment of uncontrolled formation of intravascular fibrin clots, which are capable of selective dissolution of pathological nascent clots formed intravascularly, with minimal risk of unwanted dissolution of pre-existing hemostatic clots, are provided wherein fibrinolytic or anticoagulant drugs are biocompatibly coupled to red blood cell carriers.

1 Claim, No Drawings

OTHER PUBLICATIONS

Muzykantov et al., "Fast lysis by complement and uptake by liver of avidin-carrying biotinylated erythrocytes", Int. J. Artif. Organs 1992 15 (10) :622-627.

Muzykantov et al., "Avidin acylation prevents the complement-dependent lysis of avidin-carrying erythrocytes", Biochem. J. 1991 273:393-397.

Muzykantov et al., "Tannin-Mediated Attachment of Avidin Provides Complement-Resistant Immunoerythrocytes That Can Be Lysed in the Presence of Activator of Complement", Anal Biochem. 1993 208:338-342.

Muzykantov et al., "Immunotargeting of erythrocyte-bound streptokinase provides local lysis of a fibrin clot", Biochimica et Biophysica Acta 1986 884:335-362.

Muzykantov et al., "Immunotargeting of antioxidant enzymes to the pulmonary endothelium", Proc. Natl. Acad. Sci. USA 1996 93:5213-5218.

Narita et al., "Two Receptor Systems Are Involved in the Plasma Clearance of Tissue-type Plasminogen Activator (t-PA) In Vivo", J. Clin. Invest. 1995 96:1164-1168.

Pardridge et al., "Vector-mediated delivery of a polyamide ("peptide") nucleic acid analogue through the blood-brain barrier *in vivo*", Proc. Natl. Acad. Sci. USA 1995 92:5592-5596.

Plow et al., "The cell biology of the plasminogen system", FASEB J. 1995 9:939-945.

Poznansky M. and R. Juliano, "Biological Approaches to the Controlled Delivery of Drugs:A Critical Review", Pharmacol. Rev. 1984 36:277-324.

Reilly et al., "Both Circulating and Clot-Bound Plasminogen Activator Inhibitor-1 Inhibit Endogenous Fibrinolysis in the Rat", Arterioscl. Thromb. 1991 11:1276-1286.

Sakharov D. and D. Rijken, "Superficial Accumulation of Plasminogen During Plasma Clot Lysis", Circulation 1995 92:1883-1890.

Samokhin et al., "Red blood cell targeting to collagen-coated surfaces", FEBS 1983 154 (2) :257-261.

Schnaper et al., "Plasminogen Activators Augment Endothelial Cell Organization In Vitro by Two Distinct Pathways", J. Cellular Physiology 1995 165:107-118.

Wilchek M. and E. Bayer, "The Avidin-Biotin Complex in Bioanalytical Applications", Anal. Biochem. 1988 171:1-32.

COMPOSITIONS AND METHODS FOR SELECTIVE DISSOLUTION OF NASCENT INTRAVASCULAR BLOOD CLOTS

INTRODUCTION

This application is a continuation-in-part of U.S. application Ser. No. 10/253,518, filed Sep. 23, 2002, which is a divisional of U.S. application Ser. No. 09/454,666, filed Dec. 3, 1999, now issued as U.S. Pat. No. 6,488,927, which is a continuation-in-part of PCT Application PCT/US99/10547 filed May 12, 1999, which claims the benefit of priority from U.S. Provisional Application Ser. No. 60/086,262 filed May 21, 1998.

BACKGROUND OF THE INVENTION

Occlusions of blood vessels by intravascular clots cause or/and contribute to the pathogenesis of a variety of disease conditions including myocardial infarction, stroke and pulmonary embolism and thus represent a significant medical problem. Although fibrinolytics, such as plasminogen activators, have recently been used in the treatment of some of these diseases or conditions, their effectiveness and safety are still of great concern, especially under specific prothrombotic conditions such as deep vein thrombosis and pulmonary embolism.

Pulmonary thromboembolism, a leading cause of mortality, is most often a complication of deep venous thrombosis. Statistics show that more than 95% of pulmonary emboli result from thrombi in the deep venous system of the lower extremities. Despite advances in medicine, the incidence and/or recognition of embolism and deep vein thrombosis appears to be increasing. This increase has been attributed to higher survival of trauma patients, an increase in orthopedic surgeries for joint replacement, and the widespread use of indwelling catheters, as well as the overall increase in medical and surgical procedures, particularly in older patients. As a result, methods of preventing and treating deep vein thrombosis are required to reduce the incidence of pulmonary embolisms.

Factors which promote deep vein thrombosis were defined as early as the nineteenth century and include stasis, abnormalities of the blood vessel wall, and alterations in the blood coagulation system. The highest risk groups for deep vein thrombosis are surgical patients requiring 30 minutes or more of general anesthesia, postpartum patients, patients with right and left ventricular failure, patients with fractures or injuries involving the lower extremities, patients with chronic deep venous insufficiency of the legs, is patients on prolonged bed rest, cancer patients, obese individuals, and patients using estrogens. Treatment of deep vein thrombosis most often involves use of an anticoagulant such as heparin. Even with this well-known drug, however, there is no consensus regarding the optimum regimen of anticoagulant therapy that affords both safety and efficacy. In addition to anticoagulant therapy, thrombolytic agents, such as streptokinase and urokinase, have been used in the management of acute deep vein thrombosis.

Acute vascular occlusion by fibrin thrombi is also a common and dangerous complication of surgery. Development of venous (e.g., pulmonary embolism) and arterial (e.g., arterial re-occlusion) thrombi that may embolize vitally important blood vessels increases peri-operative morbidity and mortality. Cardiopulmonary bypass surgery, transcutaneous coronary angioplasty and carotid endarterectomy and other interventions may be complicated by formation of small blood clots, which embolize to cerebral vessels and cause serious persistent neurological disorders.

In contrast to settings where ischemia is the sole threat to health (e.g., acute myocardial infarction, AMI), the management of thrombosis in the surgical settings is complicated by the added risk of bleeding at and around the wound site imparted by anti-thrombotic therapy itself. Also, in contrast with AMI, where lysis of the mature clot occluding a single vessel is a primary goal for the fibrinolytic intervention (therapy), the goal of the post-surgical anti-thrombotic management is to maintain an adequate blood flow in diverse vascular areas at risk of occlusion by post-surgical clots (prophylaxis). In the surgical settings, the ideal thromboprophylactic agent effectively dissolves nascent pathological thrombi developed in a post-operative and recovery periods, while not dissolving hemostatic fibrin clots formed during and immediately after the operation.

In addition to the objective inadequacies of existing agents (see below), widespread use of thromboprophylaxis in surgical settings continues to receive limited enthusiasm for additional reasons. The clinical significance of silent thrombotic events (pulmonary and brain micro-embolism) is under-appreciated because the symptoms may be delayed in onset and attributed to other causes, while significance of bleeding is acutely evident in the surgical practice and frequently blamed on thromboprophylaxis.

Current approaches afford some measure of protection, but all have a limited benefit/risk ratio in the surgical setting. Mechanical filters trap large clots, but cannot be used to prevent arterial re-occlusion or cerebral micro-emboli. Anticoagulants (e.g. low molecular weight heparin) reduce the incidence of thrombosis in some vascular beds, but dosing is limited by the risk of post-operative bleeding. Heparin has been reported to increase the incidence of wound hematomas, which in turn may predispose to wound infection and dehiscence. Aspirin and anti-GPIIb/IIIa agents suppress platelet aggregation, but cannot prevent formation of fibrin monomers and clot propagation. In addition to serious side effects (in part discussed above), each particular anticoagulant agent inhibits one specific mechanism for formation of clots (e.g., activation of platelets or fibrin formation), but none affords 100% fidelity of anti-thrombotic protection. A modality to dissolve nascent pathological thrombi, formed even despite anti-coagulation or due to its inapplicability, is acutely needed.

Plasminogen activators (PA's) are effective thrombolytics, which could be theoretically used for this purpose, but they have fundamental inadequacies for thromboprophylactic applications including rapid blood clearance and inactivation, non-selective degradation of the extracellular matrix and hemostatic fibrin plugs. The risk of hemorrhage practically precludes their use in the surgical settings. No existing anti-thrombotic strategy permits selective dissolution of the nascent clots without affecting pre-existing hemostatic fibrin plugs.

Streptokinase, staphylokinase, tissue-type plasminogen activator or tPA, and urokinase are members of a family of agents known as plasminogen activators. These compounds act to dissolve intravascular clots by activating plasmin, a protease that digests fibrin. Plasminogen, the inactive precursor of plasmin, is converted to plasmin by cleavage of a single peptide bond. Plasmin itself is a nonspecific protease that digests fibrin clots as well as other plasma proteins, including several coagulation factors.

Fibrinolytic therapy with plasminogen activators have been shown to be useful in the treatment of myocardial infarction and stroke. However, application of these agents to dissolution of clots formed or lodged in other vascular areas such as deep venous areas is limited by extremely rapid elimination and inactivation after bolus dosing (Plow, E. et al. 1995. *FASEB J.* 9:939–945; Narita, M. et al. 1995. *J. Clin. Invest.* 96:1164–1168). Both tPA and urokinase undergo rapid inactivation by a circulating plasminogen activator inhibitor and plasmin itself is inactivated by a circulating glycoprotein, α-2-antiplasmin (Collen, D. 1996. *Circulation* 93:857–865; Reilly, C. et al. 1991. *Arterioscl. Thromb.* 11:1276–1286). α-2-antiplasmin inactivates staphylokinase, while streptokinase is more resistant to this endogenous glycoprotein inhibitor (Collen, B. et al. 1993. *Eur. J. Biochem.* 216:307–314). Although therapeutic doses of plasminogen activators can overwhelm the potential inhibitory activity of plasminogen activator inhibitor and α-2-antiplasmin, other inhibitors of plasminogen activators also are present (C1-inhibitor, α-2-macroglobulin, antitrypsin) and contribute to the decrease over time in the fibrinolytic response upon treatment with plasminogen activators (Collen, D. 1996. *Circulation* 93:857–865). Such inactivation, or degradation of plasminogen activators and plasmin reduce the effectiveness of thrombolytic therapy and thus fail to prevent re-occlusion of blood vessels.

To overcome this problem, attempts have been made to infuse plasminogen activators intravenously for prolonged periods of time with little success; failure was attributed to the harmful side effects such as bleeding, dissolution of hemostatic clots as well as nascent clots causing deleterious consequences, and uncontrolled tissue proteolysis that occurred after extravascular deposition of plasminogen activators.

Accordingly, several different approaches have been attempted to improve efficacy of these agents in deep vein thrombosis including: prolongation of the half-life of plasminogen activators in blood; protection of plasminogen activators from inactivation by inhibitors; and targeting plasminogen activators to fibrin and thrombi. For example, chemical modifications and incorporation of plasminogen activators into liposomes have been used to prolong the half-life of plasminogen activators in the circulation (Kajihara, J. et al. 1994. *Biochim. Biophys. Acta* 1199:202–208; Heeremans, J. et al. 1995. *Thromb. Haemost.* 73:488–494). However, these studies have shown that the activity of liposome-encapsulated plasminogen activators is strongly compromised by steric limitations. Genetically engineered tPA compounds have also been produced which possess altered pharmacokinetic properties, enhanced resistance to inhibitors, and higher fibrinolytic potency (Collen, D. 1996. *Circulation* 93:857–865; Collen, D. 1993. *Lancet* 342:34–36; Krishnamurti, C. et al. 1996. *Blood* 87:14–19; Lijnen, R. and D. Collen. 1992. *Ann. NY Acad. Sci.* 667: 357–364). Several laboratories have explored conjugation of plasminogen activators with antibodies recognizing fibrin or activated platelets in order to localize plasmin generation to the clot (Holvoet, P. et al. 1993. *Circulation* 87:1007–1016; Runge, M. et al. 1996. *Circulation* 94:1412–1422; Fears, R. and G. Poste. 1994. *Fibrinolysis* 8:203–213). However, such conjugated plasminogen activators with affinity for clot components only bind to the superficial layer of the clot and do not enter into the clot interior (Sakharov, D. and D. Rijken. 1995. *Circulation* 92:1883–1890). In addition, clots bind only a small fraction of injected "fibrin-specific" plasminogen activator because of limited surface area of the formed clots. Such targeting also fails to distinguish nascent clots with deleterious consequences from pre-existing desired hemostatis clots.

Further, to date, none of these methods for modifying plasminogen activators prevent deposition of plasminogen activators in tissues, which can lead to an increase in harmful side effects; they all represent molecules or molecular complexes with sizes that do not exceed that of blood proteins. Such deposition leads to plasmin activation in tissues. Activated plasmin degrades the extracellular matrix, thus causing vascular remodeling, abnormal elevation of vascular permeability and even partial denudation of sub-endothelium (Plow et al. 1995. *FASEB J.* 9:939–945; Shreiber et al. 1995. *J. Cell. Physiol.* 165:107–118).

Accordingly, there is a need for methods of modifying plasminogen activators which not only decrease the rate of elimination and degradation of the plasminogen activators, but also prevent deposition of the plasminogen activator in the extravascular tissues. Further, compositions and methods are needed which selectively target nascent clots from within, while having minimal effects on pre-existing hemostatic clots.

Red blood cells (RBCs) normally have a life span of 120 days and thus can serve as natural carriers for drugs and biomolecules. Autologous RBCs can be easily obtained from the patient's blood, loaded with drug, and re-injected. RBCs have been used as carriers for drugs loaded into the inner volume of RBCs (Poznansky, M. and R. Juliano. 1984. *Pharmacol. Rev.* 36:277–324; Kirch, M. et al. 1994. *Biotechnol. App. Biochem.* 19:331–363; Kinoshita, K. and T. Tsong. 1978. *Nature* 272:258–260). In addition, methods for conjugation of proteins to RBCs have been developed, including methods using a streptavidin-biotin pair as a cross-linker.

Streptavidin is a 60 kDa protein that possesses four high affinity biotin binding sites and the streptavidin-biotin pair is widely used in biomedicine as a cross-linking agent (Wilchek, M. and E. Bayer. 1988. *Anal. Biochem.* 171: 1–32). Several groups have reported application of streptavidin-biotin technology in vivo for gamma-immunoscintigraphy (Kalofonos, H. et al. 1990. *J. Nucl. Med.* 31:1791–1796) and drug targeting (Pardridge, W. et al. 1995. *Proc. Natl. Acad. Sci. USA* 92:5592–5596; Muzykantov, V. et al. 1996. *Proc. Natl. Acad. Sci. USA* 93:5213–5218). Moreover, streptavidin induces no known harmful reactions in animals or humans (Kalofonos, H. et al. 1990. *J. Nucl. Med.* 31:1791–1796). Biotinylation of RBCs can be accomplished in manner which has no effect on the life span and biocompatibility of these cells in vivo in animals (Susuki, T. and G. Dale. 1987. *Blood* 70:791–795; Muzykantov, V. et al. 1991. *Blood* 78:2611–2618).

Biotinylation of proteins, including plasminogen activators, without significant reduction of functional activity of the plasminogen activator has been described (Muzykantov, V. et al. 1986. *Biochem. Biophys. Acta,* 884:355–363; Muzykantov, V. et al. 1995. *Anal. Biochem.,* 226:279–287; Muzykantov, V. et al. 1996. *J. Pharm. Exp. Ther.,* 279:1026–1034). In in vitro studies, polyvalent conjugation of various biotinylated proteins such as antibodies, enzyme peroxidase and fibrinolytic streptokinase with streptavidin conjugated-biotinylated RBCs (SA/b-RBC) was performed and high functional activity of these proteins bound to SA/b-RBC in vitro was reported (Muzykantov, V. et al. 1985. *FEBS Lett.* 182:62–66; Muzykantov, V. et al. 1986. *Biochim. Biophys. Acta* 884:355–363; Muzykantov, V. et al. 1987. *Am. J. Pathol.* 128:226–234).

However, polyvalent conjugation of biotinylated proteins to b-RBCs via streptavidin cross-linker profoundly compromises the biocompatibility of the carrier RBC. Binding of streptavidin to b-RBC leads to elimination of homologous restriction of both classical and alternative pathways of the complement thereby causing lysis of SA/b-RBC in the plasma (Muzykantov, V. et al. 1991. *Blood* 78:2611–2618; Muzykantov, V. et al. 1992. *Int. J. Artif. Organs* 15:620–627; Muzykantov, V. et al. 1993. *FEBS Lett.* 318:108–112). Streptavidin-induced cross-linking and membrane redistribution of the complement inhibitors, DAF and CD59, in biotinylated RBC membrane represents the likely mechanism for complement activation and lysis (Muzykantov, V. et al. 1992. *Biochim. Biophys. Acta* 1107:119–125; Zaltzman, A. et al. 1995. *Biochem. J.* 305:651–656). In addition, fixation of C3b complement component has been shown to lead to an increased rate of elimination of SA/b-RBC from the bloodstream via hepatic and splenic uptake (Muzykantov, V. et al. 1992. *Int. J. Artif. Organs* 15:620–627; Muzykantov, V. et al. 1996. *Anal. Biochem.* 214:109–119). Accordingly, drugs polyvalently conjugated to an RBC carrier via streptavidin can not be delivered to their targets in vivo.

This lack of biocompatibility of SA/b-RBC carrier can be overcome through modifications of the conjugation method. For example, monovalent coupling of streptavidin to b-RBCs has been demonstrated to produce a serum-stable carrier SA/b-RBC capable of binding up to $10^5$ molecules of a biotinylated model protein per RBC (Muzykantov, V. et al. 1991. *Biochem. J.* 273:393–397; Muzykantov, V. et al. 1992. *Biochim. Biophys. Acta* 1107:119–125; Muzykantov, V. et al. 1993. *Anal. Biochem.* 208:338–342; Muzykantov, V. and R. Taylor. 1994. *Anal. Biochem.* 223:142–148; Muzykantov, V. et al. 1996. *Anal. Biochem.* 214:109–119;). B-RBC carrier, monovalently conjugated with a model biotinylated protein (b-IgG) via streptavidin, circulated for at least a day as a stable complex after intravenous injection in animals, with no evidence of lysis or hepatic uptake (Muzykantov, V. et al. 1996. *Anal. Biochem.* 214:109–119). In these studies, it was also found that the half-life b-IgG monovalently conjugated with SA/b-RBCs significantly exceeded that of non-conjugated b-IgG (Muzykantov, V. et al. 1996. *Anal. Biochem.* 214:109–119).

As shown herein, monovalent conjugation of a biotinylated plasminogen activator to a SA/b-RBC carrier results in prolonged circulation of the plasminogen activator in the bloodstream and decreased deposition of the plasminogen activator in the tissues. Further, as shown herein, monovalent conjugation of biotinylated soluble receptor for urokinase plasminogen activator, (b-suPAr), and monovalent conjugation of biotinylated tissue plasminogen activator, (tPA), to a SA/b-RBC carrier results in prolonged circulation of these biotinylated plasminogen activators in the bloodstream in a form of the receptor/RBC complex (b-suPAr/SA/b-RBC complex) and the tPA/RBC complex, respectively. Moreover, as shown herein b-suPAr/SA/b-RBC complex retains its ability to bind single chain urokinase plasminogen activator (scuPA) even after prolonged circulation in the bloodstream and non-covalent binding of this fibrinolytic precursor (scuPA) to the receptor conjugated to RBC carrier (i.e., to b-suPAr/SA/b-RBC complex) leads to scuPA activation and greater resistance to plasma inhibitors and thus provides increased fibrinolytic activity on the clot itself. As also shown herein pulmonary vascular uptake of tPA is increased by crosslinking tPA to biotinylated RBC to form a tPA/RBC complex, with the increase seen to a level that exceeds the level of tPA/RBC complex in larger blood vessels. In addition, conjugation of tPA and suPAr with a monoclonal antibody against human CR1 is shown herein to promote specific coupling of fibrinolytically active anti-thrombotic agents to red blood cells, limiting the non-specific binding and tissue uptake of the complexes.

Further, as shown herein coupling of an anti-thrombotic agent to a carrier such as an RBC alters is fibrinolytic profile rendering the anti-thrombotic agent relatively impermeable to pre-formed (hemostatic) clots and extravascular tissues, thereby reducing the risk of bleeding, while prolonging its circulation and ability to be incorporated inside nascent intravascular clots, providing their fast lysis from within.

Accordingly, the present invention relates to compositions comprising a therapeutic agent, such as an anti-thrombotic agent, biocompatibly coupled to a carrier sized to inhibit penetration into existing clots, such as a red blood cell, and methods of using these compositions in the selective dissolution of nascent intravascular blood clots while avoiding lysis of pre-existing (hemostatic) clots.

SUMMARY OF THE INVENTION

An object of the present invention is to provide compositions comprising a therapeutic agent, preferably an anti-thrombotic agent, more preferably a fibrinolytic, biocompatibly coupled to the surface of a carrier similar in size to a red blood cell, which circulate for a prolonged time and selectively dissolve nascent intravascular blood clots. In a preferred embodiment, the carrier comprises a red blood cell. Coupling is preferably accomplished by cross-linking a biotinylated therapeutic agent to a biotinylated carrier such as a red blood cell via streptavidin. Alternatively, a therapeutic agent is conjugated with molecules with high affinity to a specific red blood cell surface protein such as monoclonal antibodies which then bind specifically with red blood cells upon administration. An example of a monoclonal antibody specific for a red blood cell carrier is a monoclonal antibody against human CR1.

Another object of the present invention is to provide a method of preventing and treating uncontrolled formation of nascent intravascular clots while avoiding lysis of pre-existing (hemostatic) clots in a patient which comprises administering to a patient suffering from uncontrolled formation of intravascular clots a composition comprising a therapeutic agent such as an anti-thrombotic agent biocompatibly coupled to a carrier similar or greater in size to a red blood cell. In a preferred embodiment the carrier comprises a red blood cell.

DETAILED DESCRIPTION OF THE INVENTION

The present invention provides compositions and methods for prevention and treatment of deep vein thrombosis, pulmonary embolism and other diseases or syndromes characterized by uncontrolled formation of intravascular fibrin clots. The invention is based on the biocompatible coupling of a therapeutic agent, preferably an anti-thrombotic agent, more preferably a plasminogen activator, to a carrier similar in size to a red blood cell (RBC). Preferably the carrier is a RBC. RBC carriers or carriers similar in size to RBCs (3–5 microns) provide for prolonged circulation, restricted tissue uptake and minimal permeation into clots of the drug. The monovalent conjugation of plasminogen activators to biotinylated RBCs via streptavidin (referred to herein as SA/b-RBC) serves as an example in the present invention of a biocompatible coupling method. Biotinylated plasminogen activators are referred to herein as b-PAs. Another example of biocompatible coupling is the crosslinking of plasminogen activators to biotinylated molecules such as monoclonal antibodies which then couple specifically with a is carrier such as red blood cells in whole blood. An example of an antibody useful in this coupling method is a monoclonal antibody against human CR1.

Experiments were performed to examine the conjugation of b-PAs to biotinylated RBCs via streptavidin. Results of in vitro tests showed that streptavidin provided specific and effective conjugation of the b-PAs to the biotinylated RBC (Table 1).

TABLE 1

Number of $^{125}$I-coupled Plasminogen Activator Molecules Per Red Blood Cell

| Plasminogen Activator | # Coupled to Biotinylated RBCs | # Coupled to SA/ biotinylated RBCs |
|---|---|---|
| biotinylated-scuPa | <400 | 79,000 |
| biotinylated-tPA | <400 | 30,000 |
| biotinylated-urokinase | <1200 | 42,000 |
| biotinylated-streptokinase | <300 | 12,000 |

When tested in a fibrin plate lysis assay and in an assay of release of radiolabeled iodine from a fibrin clot (formed from $^{125}$I-fibrinogen), the b-PA/SA/b-RBC conjugates were shown to be stable and to display high fibrinolytic activity. When the b-PA/SA/b-RBC conjugates were added to solution of $^{125}$I-fibrinogen before formation of fibrin clot, the subsequent fibrinolysis attained 71±12%. Non-conjugated PAs induced 96±5.5% lysis of fibrin clot. Thus, conjugation of b-PA to SA/b-RBC does not compromise significantly fibrinolytic activity of PA.

The half-life (i.e., rate of degradation and elimination from blood) of RBC-conjugated plasminogen activators was also examined in vivo in rats. The kinetics of blood clearance of $^{125}$I-scuPA, $^{125}$I-urokinase, $^{125}$I-streptokinase, or $^{125}$I-tPA were determined following intravenous injection of scuPA or tPA at a dose of 5 µg/kg. Within one hour of injection, the blood level of scuPA dropped to less than 5% of the injected dose. In contrast, the blood level of SA/b-RBC-conjugated scuPA was 10-fold higher at the one hour time point, and remained at high levels (20% of injected dose) for up to 24 hours. Similar results were seen with tPA, urokinase and streptokinase. Pharmacokinetic analysis of the areas below the curves of blood level of plasminogen activators versus those biocompatibly coupled to RBCs during 24 hours after intravenous injection revealed that the half-life of RBC-conjugated PAs exceeded that of non-conjugated PAs by several orders of magnitude.

Further, conjugation of the biotinylated plasminogen activators with SA/b-RBC carrier did not cause intravascular lysis of the carrier RBC labeled with $^{51}$Cr and did not change the biodistribution of RBC in any tissues except the spleen. Splenic uptake of the b-PA/SA/b-RBC was elevated about 4-fold. However, such increases in splenic uptake of chemically modified RBCs are well known in the literature. Importantly, after injection of b-PA/SA/b-RBC conjugates, tissue uptake of plasminogen activators was markedly reduced. For example, level of $^{125}$I-tPA in the brain tissue (expressed as percentage of that in the blood) was 18.3±1.1%, whereas that parameter for $^{125}$I-b-tPA/SA/b-RBC was 1.8±0.5%. Thus conjugation with an RBC carrier provides ten fold reduction of the uptake in the brain.

In the case of tPA, the tissue distribution data revealed that conjugation of tPA to RBC not only prolonged its bioavailability in the circulation, but also dramatically increased its pulmonary vascular uptake. One hour after injection, 20% of the radiolabeled tPA was found in the lungs of rats injected with $^{125}$I-tPA/RBC, a value that is 100-fold higher than what is seen following injection of soluble $^{125}$I-tPA. Yet, the pulmonary uptake of tPA/$^{51}$Cr-RBC was only marginally higher than that of non-modified RBC (3.8% versus 1.2%). Thus, the lungs of rats injected with tPA/RBC contained five-fold more radiolabeled tPA than radiolabeled RBC, whereas the ratio of radiolabeled tPA to radiolabeled RBC equaled one in all other tissues, including blood. This indicates that there was a significant transfer of tPA to the lung, the pulmonary vasculature, a result that was not seen in other organs (an organ-specific effect). This transfer of tPA from the carrier RBC occurred rapidly and lasted for several hours. In addition, the lung to blood ratio of $^{125}$I-tPA/RBC was 20 times higher than that of radiolabeled tPA whereas in the kidney, brain and heart, these organ to blood ratios were ten times lower, data indicating that coupling of tPA to RBC strongly restricted uptake by organs other than the lung.

Experiments were also performed to determine strategies for activating inactive plasminogen activators in blood. The soluble form of urokinase receptor (suPar) has been reported to bind scuPA and convert inactive scuPA to an active uPA, as well as protect it from inhibition by plasma inhibitors (Higazi, A. et al. 1995. *J. Biol. Chem.* 270: 17375–17380; Higazi, A. et al. 1996. *Blood* 87:3545–3549). The half-life of suPAr in blood, however, is short, in the range of minutes following intravenous injection. Accordingly biotinylated suPAr was coupled to SA/biotinylated RBCs to prolong the half-life of suPAr in vivo. This coupling yielded a complex designated as b-suPAr/SA/b-RBC that possessed up to $1.3 \times 10^5$ molecules of suPAr per SA/b-RBC molecule. Without streptavidin conjugated to the biotinylated RBCs, the binding of suPAr to the RBC carrier was an order of magnitude lower ($1.2 \times 10^4$ suPAr molecules/RBC).

The ability of b-suPAr/SA/b-RBC complex to bind single chain urokinase plasminogen activator (scuPA) was examined in vitro by incubating $^{125}$I-labeled scuPA with b-suPAr/SA/b-RBC or intact RBCs (used as a control of non-specific binding of scuPA). It was found that $1.5+0.1 \times 10^4$ molecules of $^{125}$I-scuPA per b-suPAr/SA/b-RBC bound while only $0.06+0.01 \times 10^4$ $^{125}$I-scuPA per RBC bound. Thus, the b-suPAr/SA/b-RBC complex binds scuPA effectively and specifically.

The fibrinolytic activity of the scuPA associated with b-suPAr/SA/b-RBC complex (scuPA/b-suPAr/SA/b-RBC) was then examined. Fibrin clots were prepared that contained $^{125}$I-fibrin and either phosphate-buffered saline (control clots), RBC carrier alone, b-scuPA/SA/b-RBC complexes, scuPA/b-suPAr/SA/b-RBC complexes, or scuPA alone. In control clots, less than 5% of the radiolabel was released to the supernatant after 120 minutes incubation at 37° C. Neither RBC carrier alone nor b-scuPA/SA/b-RBC complexes (b-scuPA conjugated to SA/b-RBC directly) caused detectable fibrinolysis. Free scuPA caused about 10% fibrinolysis. However, similar doses of scuPA/b-suPAr/SA/b-RBC complexes caused 95±4% fibrinolysis. These results indicate that binding of scuPA to b-suPAr conjugated with SA/b-RBC indeed stimulates fibrinolytic activity of scuPA and that b-suPAr/SA/b-RBC complex is active as a fibrinolytic agent.

To determine the fate of the b-suPAr/SA/b-RBC complex in vivo, rats were injected intravenously with $^{125}$I-suPAr/SA/$^{51}$Cr-b-RBC and the blood levels and biodistribution of the complex were studied. Conjugation of suPAr to the carrier RBC significantly increased the half-life of suPAr in the bloodstream. The blood level of non-conjugated suPAr was undetectable within 3 hours, while 20% of the b-suPAr/SA/b-RBC complex was measurable out to 24 hours after injection.

Biodistribution studies showed that conjugation of suPAr did not lead to hemolysis or to reticuloendothelial uptake of the carrier RBC. In fact, distribution of the conjugated b-suPAr/SA/$^{51}$Cr-b-RBC was similar to that of the control $^{51}$Cr-RBC distribution. One hour after injection of rats with b-suPAr/SA/$^{51}$Cr-b-RBC, blood samples were obtained for determination of binding of $^{125}$I-scuPA to blood cells. Blood obtained from rats injected with the b-suPAr/SA/b-RBC complexes bound three times more scuPA than blood obtained from control animals. These data indicate that b-suPAr/SA/b-RBC is functionally active in the circulation and is capable of binding scuPA. Quantitation of the binding revealed that, after circulating for one hour in the bloodstream, each b-suPAr/SA/b-RBC complex binds approximately $10^4$ molecules of scuPA. This value is similar to the initial levels of scuPA binding of b-suPAr/SA/RBC before injection in rats. Therefore, circulation in the bloodstream did not alter the binding ability of this complex.

The fibrinolytic activity of crosslinked plasminogen activators was examined in vivo in rats. Rats were injected intravenously with either 250 μg of unconjugated tPA or 50 μg of tPA conjugated to carrier RBC and blood was collected after 10, 60 and 180 minutes. $^{125}$I-fibrinogen was added to all samples and blood was allowed to coagulate at room temperature. Neither tPA nor tPA/RBC suppressed clot formation at the test concentrations, an important consideration in terms of safety of the present invention. The clots were then incubated at 37° C. and the rate of clot lysis was examined. Spontaneous fibrinolysis did not exceed 10% at either 10 minutes or 60 minutes in rats injected with saline. Fibrinolysis was augmented 10 minutes after injection of unconjugated tPA. However, the rate of fibrinolysis in blood obtained 60 minutes after tPA injection only marginally exceeded that of the control animals, as was expected in light of the rapid elimination of tPA from blood. Remarkably, blood obtained even 3 hours after tPA/RBC injection retained significant fibrinolytic activity (40% clot lysis), even though the injected dose of tPA was 5-fold lower. These data show that conjugation of tPA to the carrier RBC significantly increased the circulation of enzymatically active plasminogen activator in vivo and prolonged the in vivo half-life of the plasminogen activator in blood to a level that would overcome any steric limitations that might be imposed by conjugation to RBC.

Experiments were also performed with mouse RBCs. In these experiments, tPA was conjugated to washed murine RBC in Krebs-Ringer buffer containing glucose and 3% bovine serum albumin to minimize energy depletion and mechanical damage. Using methods as described for rat RBCs, 3 to $4\times10^4$ molecules of biotinylated tPA or suPAr per biotinylated murine RBC were coupled without detectable hemolysis as shown below in Table 2. In these tests, the murine RBC were biotinylated with 10 μM BxNHS in Krebs-Ringer glucose (pH 7.4). The radiolabeled activators were coupled to b-RBC via streptavidin in BSA-containing Krebs-Ringer glucose. Therefore, murine RBC were conjugated in the same way as human and rat RBCs.

TABLE 2

Coupling Efficiency of Murine RBC

| Activator | Added (per RBC) | Bound (per RBC) | % Added (of RBC) | Bound (per SA/b-RBC) | % Added (of SA/B-RBC) |
|---|---|---|---|---|---|
| $^{125}$I-b-tPA | $3 \times 10^5$ | $4.4 \times 10^3$ | 1.5% | $3.2 \times 10^4$ | 11% |
| $^{125}$I-b-suPAr | $2 \times 10^5$ | $3.5 \times 10^2$ | 0.2% | $4.1 \times 10^4$ | 20% |

Studies were then performed to examine the transfer of tPA from its carrier RBC to tissue, specifically vascular tissue. As a model for pulmonary vasculature transfer, human umbilical vein endothelial cells (HUVEC) cells were used in culture. RBC carriers were constructed by the method of the present invention. The RBCs carried either no protein (naive RBC), tPA (tPA/RBC, suPAr (suPAr/RBC), scuPA conjugated to suPAr molecules (scuPA-suPAr/RBC), scuPA (scuPA/RBC), or anti-TM/RBC. RBC carrying the protein molecules ($3\times10^4$ molecules/RBC) were incubated with HUVEC ($2\times10^7$ RBC per well, 160 minutes at 37° C.). Non-bound cells were eliminated by gentle washing with a phenol-free medium and 1 ml of water was added to lyse bound RBC. The number of HUVEC-bound RBC was determined by measuring the absorbance at 405 nm emitted by hemoglobin released into the cell lysates and expressed as 1,000 RBC/well. The results are shown in Table 3.

TABLE 3

Adhesiveness of complexes to endothelium in culture

| | Naive RBC | tPA/RBC | suPAr/RBC | scuPA-suPAr/RBC | scuPA/RBC | anti-TM/RBC |
|---|---|---|---|---|---|---|
| RBC bound | 2.6 | 1.7 | 2.5 | 2.3 | 22 | 11 |

Neither tPA/RBC, suPAr/RBC, nor scuPA-suPAr/RBC were adhesive to HUVEC, as evidenced by binding levels comparable to naive RBC. In contrast, scuPA/RBC complex or RBC conjugated with antibody against endothelial surface glycoprotein, thrombomodulin (used as a positive control) were highly adhesive. Accordingly, complexes comprising a soluble form of urokinase receptor biocompatibly coupled to a red blood cell carrier minimize the potential hazardous interactions of urokinase with endothelial cells.

Next, $^{125}$I-tPA/RBC were incubated with HUVEC, the unbound RBC removed by washing and $^{125}$I in the wells measured. HUVEC bound $8.1+0.2\times10^9$ molecules tPA/well after incubation with $^{125}$I-tPA/RBC. The results shown in Table 3 indicate that only 5% of this amount of cell-bound $^{125}$I-tPA was attributable to RBC-associated tPA in the wells ($3\times10^4$ molecules $^{125}$I-tPA/RBC$\times1.7\times10^3$ RBC/well=$5.1\times10^8$ molecules RBC/$^{125}$-tPA/well). Therefore, tPA transfers from RBC to HUVEC, demonstrating the successful use of the RBC carrier of the instant invention.

Accordingly, the present invention provides novel compositions for prolonging the half-life of therapeutic agents including anti-thrombotic agents such as plasminogen activators and anticoagulants in the bloodstream of animals including humans by decreasing the degradation and elimination of the therapeutic agents in the bloodstream.

The present invention also provides a method for increasing selective dissolution of blood clots by therapeutic agents such as anti-thrombotics in blood of a patient which comprises administering to a patient a composition comprising a therapeutic agent, preferably an anti-thrombotic agent, more preferably a plasminogen activator, biocompatibly coupled to a red blood cell carrier or a carrier similar in size to a red blood cell.

Further, as demonstrated herein, coupling of an anti-thrombotic agent such as a fibrinolytic or anticoagulant drug to a carrier similar in size to a red blood cell, i.e., a carrier approximately 3–5 microns also results in a composition that selectively dissolves pathological, nascent blood clots such as formed after surgical interventions, while minimizing the risk of untoward dissolution of hemostatic pre-existing clots.

Fibrin clots undergo a rapid maturation process, which includes mechanical retraction, incorporation of pro-thrombotic moieties and cross-linking by Factor XIII transglutaminase, all markedly limiting its porosity. Thus, established surgical clots and extravascular hemostatic fibrin in the wound are likely to be far less permeable to blood components than are nascent intravascular clots.

Once surgical hemostasis has been attained, the risk of post-operative bleeding would be lessened if a plasminogen activator (PA) could be delivered in a manner that limits its penetration into existing clots, but permits inclusion into the nascent clots. One means to achieve this goal is to link a plasminogen activator to a large carrier of, for example 3–5 microns, such as red blood cells (RBC). Coupling to RBC would restrict the physical penetration of PA into physiological clots and prolong its survival. This mechanism of delivering PA may permit prophylactic administration once surgical hemostasis has been secured.

In these experiments, the anti-thrombotic agent tissue plasminogen activator (tPA) was coupled to RBCs using strepatividin(SA) biotin as a cross linker. The amount of biotinylated tPA ($_b$tPA) that can be coupled to biotinylated rat, mouse or human RBCs ($_b$RBC) ranges from $10^5$ molecules/RBC to less than 200 molecules of non-biotinylated tPA. Attachment to $_b$RBC using polyvalent streptavidin inactivated the complement controlling proteins DAF and CD59, leading to hemolysis of $_b$RBC/SA in autologous serum. However, RBC biotinylated in biotin ester levels below 100 μM ($_{bx}$RBC activity, wherein X≦100) do not activate complement and are stable in fresh homologous serum.

The activity of $_{b10}$RBC/SA/$_b$tPA complexes possessing 6.5–7.5×10$^5$ tPA molecules per RBC was tested in fibrin clots formed by adding thrombin to $^{125}$I-labeled fibrinogen as described by Murciano et al. (Am. J. Physiol. Lung Cell Mol. Physiol 2002 282:L529–539). Clots invested with RBC/tPA were dissolved releasing $^{125}$Iodine into the supernatant. Similar results were observed with clots formed from rat, mouse and human plasma using tPA coupled to homologous RBCs. During a 24 hour incubation period in fresh serum at 37° C., hemolysis of RBC/tPA by complement was comparable to control RBCs and only a minor fraction of tPA detached from the RBCs.

Dissolution of pre-existing versus nascent fibrin clots by free tPC and RBC/tPA was first compared in vitro. Free tPA caused 50% dissolution of pre-existing versus 90% lysis of nascent clots (1.9 fold difference). In contrast, tPA when coupled to a large carrier of, for example 3–5 microns such as an RBC, caused less than 5% dissolution of pre-existing clots versus 80% dissolution of nascent clots (17-fold difference). Thus, compositions of the present invention comprising an anti-thrombotic agent coupled to a large carrier of, for example 3–5 microns such as an RBC, exhibit ten times greater selectivity toward nascent clots than anti-thrombotic agent alone.

Fibrinolytic efficacy of compositions of the present invention was also tested in a mouse model of venous thrombosis. First, experiments were performed to confirm that RBC carriage prolongs the circulation of tPA in mice. In these experiments, free $^{125}$I-tPA disappeared from the blood stream within 20 minutes while 50–60% of injected RBC/$^{125}$I-tPA remained in the blood stream 60 minutes post injection. Next, findings in rats that the duration of fibrinolytic activity in the blood after bolus injection of tPA was prolonged by RBC carriage were confirmed. Fibrinolysis of clots formed from blood taken 2 minutes after free tPA injection was facilitated, but this enhancement disappeared within 20 minutes after injection. In contrast, clots formed from blood taken 60 minutes post injection of RBC/tPA dissolved almost completely. Therefore, like rats, active RBC/tPA, but not free tPA, circulates for a prolonged time after injection in mice.

A model of pulmonary embolism induced by injecting radiolabeled fibrin microemboli 3–5 microns in diameter ($^{125}$I-ME) was used to examine fibrinolysis of intravascular clots in vivo. Momentarily after intravenous injection $^{125}$I-ME form aggregates invested with blood cells which lodge in the lungs of mice and rats (Murciano et al. Am. J. Physiol. Lung Cell Mol. Physiol. 2002 282:L529–539; Bdeir et al. Blood 200 96:1820–26). Measuring radioactivity in the lungs 1 hour after $^{125}$I-ME injection provides quantitative measurement of intravascular fibrinolysis of pulmonary emboli (Murciano et al. Am. J. Physiol. Lung Cell Mol. Physiol. 2002 282:L529–539).

Injection of free tPA 10 minutes after $^{125}$I-ME dissolved the clots almost completely. In contrast, less that 20% fibrinolysis was seen when tPA was injected even 5 minutes prior to the emboli, consistent with its rapid clearance from the bloodstream. In contrast, RBC/tPA injected after $^{125}$I-ME produced modest (less than 40%) fibrinolysis of pulmonary emboli, while RBC/tPA injected 20 minutes before $^{125}$I-ME caused 80% fibrinolysis. Thus, the ratio of fibrinolysis of nascent versus pre-existing clots was 0.2 and 2.2 for free tPA and RBC/tPA, respectively.

Large, life-threatening occlusive clots are less permeable and susceptible to fibrinolysis than microemboli due to a lower surface to mass ratio (Murciano et al. Am. J. Physiol. Lung Cell Mol. Physiol. 2002 282:L529–539). Accordingly, the thromboprophylactic ability of RBC/tPA to effectively dissolve occlusive thrombi in a large vessel was examined using the FeCl$_3$ model of carotid arterial injury. In these experiments, thrombus formation and fibrinolysis were monitored by Doppler ultrasound. Shortly after application of the FeCl$_3$ solution to the tunica adventitia, blood flow in the carotid artery was practically undetectable and the vessel remained occluded for the entirety of the experiment (60 minutes). Injection of free tPA prior to thrombus formation did not cause clot lysis or facilitate reperfusion. Neither did injection of free tPA or RBC/tPA 10 minutes after thrombus formation. However, RBC/tPA injected 10 minutes prior to thrombosis, though not affecting the rate of clot formation, began to dissolve the clots within 10–20 minutes and restored the blood flow reaching a mean of approximately 80% of baseline by 20–30 minutes. The ratio of fibrinolysis of nascent versus pre-existing clots in this model was 0.2 and 3.3 for free tPA and RBC/tPA, respectively.

Thus, these experiments are demonstrative of the thromboprophylaxic utility of compositions of the present invention. As shown herein complexing a therapeutic agent, particularly an anti-thrombotic agent such as a plasminogen activator to a large carrier of, for example 3–5 microns, such as an RBC minimizes diffusion of the anti-thrombotic agent from the vasculature and fibrinolysis of pre-existing clots, while markedly prolonging its life-span and permitting dissolution of nascent clots soon after their formation, thereby converting a anti-thrombotic agent such as a fibrinolytic into a thromboprophylactic agent. Specifically, RBC/tPA showed a 17-fold enhancement in the lysis of nascent versus pre-existing clots in vitro, likely by restricting the diffusion of tPA into fibrin. Biocompatible carriage by RBC also prolonged tPA circulation, markedly extending duration of its fibrinolytic activity in the blood providing the complex with the ability to dissolve pulmonary emboli and occlusive arterial thrombi, when infected prior, but not post thrombosis. RBC/tPA was ten times more selective than free tPA towards lysing nascent versus pre-existing pulmonary emboli and 20 times more selective towards nascent versus pre-existing arterial clots. Furthermore, prophylactic injection of RBC/tPA dissolved occlusive thrombi in the carotid artery soon after their formation, despite the fact that they proved resistant to dissolution by free tPA injected before or after thrombosis. Therefore, complexing a therapeutic agent such as an anti-thrombotic agent such as tPA to a carrier such as a RBC or a carrier similar or greater in size than a RBC converts the therapeutic agent into a potent thromboprophylactic agent.

Preparation of compositions comprising an anti-thrombotic agent and a biocompatible carrier such as red blood cell carriers is performed in accordance with known methods of conjugation and is exemplified by monovalent crosslinkage via biotin, streptavidin, and monoclonal antibodies. However, as will be obvious to those of skill in the art upon this disclosure, other methods of biocompatible coupling, i.e., chemical conjugation, non-covalent binding via a conjugated receptor, or other means of attachment which does not lead to poor biocompatibility of the carrier exemplified by lysis and increased phagocytosis could also be used.

Autologous transfusion is standard practice in elective surgery. Results from human studies exploring RBC carriage of other drugs indicate that it is technically feasible to conjugate therapeutic agents such as anti-thrombotic agents (e.g. fibrinolytic agents such as tPA) to auto-donated RBC and to re-inject the complex after surgery. Alternative bioconjugation techniques such as coupling to the RBC via activated polyethylene glycol (PEG) may enhance biocompatibility and minimize the immune response to non-autologous RBC. Coupling a therapeutic agent to RBCs via PEG may extend the applicability of the proposed strategy by generating universal donor RBC/tPA with a reasonable shelf-life. Furthermore, it is possible to couple therapeutic agents to RBCs directly in the bloodstream. Human RBC possess the complement receptor I (CRI) that binds immune complexes and transfers them to macrophages without opsonization of RBC themselves. CRI monoclonal antibodies and anti-CRI immunoconjugates injected in animals bind to RBC and circulate for a prolonged time without causing cell damage. Thus, it is expected that anti-CR1/anti-thrombotic agent conjugates can also be used for prophylaxis without the need for RBC extraction, modification or transfusion.

As will be understood by those of skill in the art upon reading this disclosure, other antibodies selective to RBCs can be used in similar fashion to anti-CRI as well. The compositions of the present invention are also expected to be safer in cerebral fibrinolysis. Free tPA improves reperfusion in ischemic stroke, but causes collateral damage in the brain in hemorrhagic stroke. In addition to unintended dissolution of hemostatic clots in the cerebral vasculature, diffusion of anti-thrombotic agents such as plasminogen activators into the brain aggravates cerebral edema and matrix remodeling, and causes direct cytotoxicity to neurons. It is believed that compositions of the present invention such as RBC/tPA will be safer due to better retention within the vascular compartment.

In a preferred embodiment, the compositions of the present invention further comprise pharmaceutically acceptable vehicles for intravenous administration to patients with a disease or condition characterized by uncontrolled intravascular fibrin clot formation including deep venous thrombosis. Such pharmaceutically acceptable vehicles include saline, phosphate buffered saline, or other liquid sterile vehicles accepted for intravenous injections in clinical practice.

As will be understood by the skilled artisan upon reading this patent application, the model anti-thrombotic agent used in these experiments, tPA, represents just one of a large number of therapeutic agents whose therapeutic profile will be enhanced or favorably altered by complexing with a large carrier of, for example 3–5 microns such as RBC carriage. Examples of such therapeutic agents include, but are not limited to anti-inflammatory agents, anti-coagulant agents such as protein C, and enzymes that inactivate toxins in the bloodstream. Compositions of the present invention are preferably administered systemically as a bolus intravenous injection of a single therapeutic dose of the drug (for example, 0.1–1.0 mg/kg for plasminogen activators). When used prophylactically, the compositions of the present invention is preferably administered to provide safe and effective thromboprophylaxis in specific surgical settings that are accompanied by a high incidence of arterial thrombosis.

For example, a few hours after angioplasty, when initial hemostatic fibrin formation is relatively mature, a patient is administered an injection of preformed tPA/RBC complex, or scuPA-suPAR/anti-CR1 conjugate which binds to the circulating RBC. The life span of RBC-bound complex in the circulation may be varied from several hours to several weeks, depending on the number of tPA or scuPA molecules on RBC. The complex has little or no access to the tissues or mature fibrin clots and circulates the bloodstream in inactive form due to physiological suppression by plasminogen. However, if nascent fibrin clots begin form intravascularly, the entire complex is incorporated, resulting in fibrinolysis in a geographically constrained area.

The following nonlimiting examples are provided to further illustrate the present invention.

EXAMPLES

Example 1

Preparation of Conjugated Plasminogen Activators—Biotinylation, Radiolabeling of Proteins, Conjugation of Proteins to RBC and Assessment of the Fibrinolytic Activity Biotin ester, 6-biotinylaminocaproic acid N-hydroxysuccinimide ester (BxNHS) was dissolved in 100% dimethylformamide to a final concentration of 10 mM or 1 mM. Tissue-type plasminogen activator (tPA), urokinase, streptokinase and soluble urokinase plasminogen activator receptor (suPAr) were biotinylated at ten-fold molar excess of BxNHS. Eight microliters of fresh 1 mM BxNHS were added to 100 µl of a protein solution (1 mg/ml in borate buffered saline, BBS, pH 8.1). After a 1 hour incubation on ice, excess of non-reacted BxNHS was eliminated by overnight dialysis. Biotinylated proteins were radiolabeled with $^{125}$Iodide using Iodogen-coated tubes according to the manufacturer's recommendations (Pierce). Incubation of 100 μg of a biotinylated protein and 100 μCi of sodium $^{125}$Iodide in a tube coated with 100 μg of Iodogen for 20 minutes on ice yielded streptavidin with a specific radioactivity of approximately 500 cpm per ng. Excess iodine was eliminated by dialysis. More than 95% of radiolabeled proteins were precipitable by TCA.

Two milliliters of fresh heparinized blood was then centrifuged at 1,500 rpm for 5 minutes and supernatant (i.e., plasma) was eliminated. The pellet was then resuspended and washed with PBS by standard centrifugation (10 ml of PBS per 1 ml of pellet, 1,500 rpm, 5 minutes, four times) to make a 100% suspension of washed RBC. PBS (0.9 ml) was then added to 0.1 ml of RBC pellet (i.e., make 10% suspension of washed RBC). One hundred microliters of 300 mM boric acid (pH 9.0) was added to 1.0 ml of 10% RBC. BxNHS in DMFA was then added to this suspension to obtain a final BxNHS concentration in the reaction mixture equal to 10 μM and to obtain $b_{10}$-RBC. At first, 1 μl of stock solution of 0.1 M BxNHS/DMFA was added to 99 μl DMFA. Then 10 μl of this fresh 1 mM BxNHS/DMFA was added to 1 ml 10% RBC and mixed well. After a 30 minute incubation with periodic gentle shaking, at 20° C., excess non-reacted BxNHS was eliminated from the reaction mixture by standard centrifugation with PBS containing 2 mg/ml BSA (BSA-PBS). A 10% suspension of biotinylated RBC in BSA-PBS was prepared.

To attach streptavidin to b-RBC, 20 μl of SA stock solution (1 mg/ml in PBS) was added to 100 μl 10% suspension of b-RBC and mixed well. This provides addition of 1 μg SA per 5×10$^6$ b-RBC (about 2×10$^6$ molecules per b-RBC). After a 30 minute incubation with periodic gentle shaking at 20° C., non-bound SA was removed by standard centrifugation in BSA-PBS.

To attach biotinylated plasminogen activator or suPAr to SA/b-RBC, 5 μl of stock solution b-PA or b-suPAr (1 mg/ml in PBS) was added to 100 μl 10% suspension of SA/b-RBC and mixed well. This provides addition of 1 μg b-PA or b-suPAr per 2×10$^7$ SA/b-RBC (about 3.5×10$^5$ molecules per SA/b-RBC). b-PA or b-suPAr was then incubated with the 10% suspension of SA/b-RBC for 1 hour (periodic gentle shaking, 20° C.). Non-bound proteins were removed by standard centrifugation with BSA-PBS. To quantitate binding of b-PA or b-suPAr to SA/b-RBC, radiolabeled b-PA or b-suPAr was used as a tracer.

Proteins were radiolabeled with $^{125}$I-Na (Perkin Elmer, Boston, Mass.) using IODOGEN (Pierce, Rockford, Ill.) and RBC were radiolabeled with $^{51}$Cr as described by Muzykantov et al. (Anal. Biochem. 1996 241:109–119).

The suspension of $^{51}$Cr-RBC/$^{125}$I-tPA in phosphate buffered saline (PBS)/3% bovine serum albumin (BSA) was stable for at least 4 days at 4° C. To test hemolysis by complement, control RBC, $_b$RBC/SA or $_b$RBC/SA/$_b$tPA were incubated in fresh serum for 1 hour at 37° C., centrifuged (5 minute, 1200 g) and the released hemoglobin was determined spectrophotometrically at 405 nm.

Example 2

In Vivo Administration of Conjugated Plasminogen Activators

To study biodistribution of radiolabeled preparations in rats, injection of 0.5 ml of saline containing 1 μg of radiolabeled PA or suPAr, or these proteins coupled to the carrier RBC, was made into the tail vein under anesthesia. To trace RBC-coupled plasminogen activators after in vivo administration, 20–50 μl of 10% suspension of $^{125}$I-b-PA/SA/b-RBC was injected via the tail vein in anesthetized rats. At indicated times after injection (5 minutes–24 hours), anesthetized rats were sacrificed by exsanguination. Blood and internal organs were collected. Organs were rinsed with saline until free of blood and weighed. Radioactivity of $^{125}$I in aliquots of blood and internal organs was then determined using a gamma-counter. Plasma was then separated from the blood by centrifugation of blood and radioactivity in the plasma was determined. Results were calculated as cpm per gram of tissue, blood or plasma, as mean±standard error (M±SE). Statistical comparisons were made using one-way analysis of equal variance (ANOVA) followed by Student-Newman-Keuls Method at a level of statistical significance of $p<0.05$.

Example 3

In Vitro Clot Lysis

Fibrin clots were formed by adding $CaCl_2$ and thrombin (20 mM and 0.2 units/ml final concentrations) to fibrinogen (3 mg/mL) trace-labeled with $^{125}$I-fibrinogen. To simulate lysis of pre-existing clots, clots were overlaid with each fibrinolytic agent or saline (control) for 20 minutes at 20° C. To lyse nascent clots, fibrinolytics were added directly to $^{125}$I-fibrinogen prior to adding $CaCl_2$ and thrombin. To initiate fibrinolysis, clots were placed at 37° C. and the radioactivity in the supernatants was measured in a gamma-counter. (Perkin Elmer, Boston, Mass.)

Example 4

RBC, tPA and RBC/tPA Circulation In Vivo $^{51}$Cr-RBC, $^{125}$I-tPA or $^{51}$Cr-RBC/$^{125}$I-tPA were injected into the tail veins of anesthetized rats or mice. At selected times 100–200 μl of blood were taken from animals into heparin, centrifuged at 1200 g and the radioactivity was measured in plasma supernatants and RBC pellets. The animals were sacrificed 1–3 hours after injection and radioactivity in the organs was analyzed in a gamma-counter.

Example 5

Dissolution of Clots Formed from Blood Obtained after Injections of tPA or RBC/tPA Control RBC, free tPA, RBC/tPA or saline (control) were injected intravenously into rats or mice. At indicated times, 100–200 μl aliquots of blood were drawn in the absence of anticoagulant, rapidly mixed with trace amounts of $^{125}$I-Fibrinogen and were allowed to clot in borositcate tubes at 20° C. After 20 min maturation, clots were overlaid with saline, incubated at 37° C. and the release of 125 Iodine was measured.

Example 6

Dissolution of Pulmonary Emboli by tPA or RBC/tPA

Suspensions of $^{125}$I-fibrin microemboli ($^{125}$I-ME) were prepared as described (Murciano, J. C. et al. 2002. *Am J Physiol Lung Cell Mol Physiol* 282:L529–539 and Bdeir, K.

et al. 2000. *Blood* 96:1820–1826) and injected into anesthetized mice. A 350 µil sample containing a 50% suspension of RBC, RBC mixed with saline or tPA (0.5 mg/Kg) or RBC/tPA after injection of $^{125}$I-ME. Animals were sacrificed 1 hr after injection of $^{125}$I-ME, the lungs were isolated, rinsed in saline and the residual radioactivity was measured in the gamma-counter.

Example 7

Dissolution on the Carotid Arterial Thrombi by RBC/tPA

We used a described murine model of acute carotid embolization (Farrehi, P. M. et al., 1998. *Circulation* 97:1002–1008). Occlusion of the vessel was determined by Doppler ultra-sound using a 0.5 VB flow probe connected to a recording system (Transonic, Ithaca, N.Y.). Complete occlusion occurred within 8–10 min of the vessel injury by FeCl3, and in control animals vessels remain occluded until the experiment was terminated at 60 min. Either before FeCl3 application or 10 n-tin after complete occlusion, 350 µil solution of PBS, RBC, tPA 0.7 mg/Kg alone or mixed with RBC, or RBC/tPA (containing 0.5 mg/Kg tPA) was injected through the opposite jugular vein.

What is claimed is:

1. A method for preferentially dissolving nascent intravascular blood clots in a subject as compared to effect on pre-existing haemostatic clots in the subject comprising administering to the subject a plasminogen activator biocompatibly coupled to a red blood cell carrier.

* * * * *